US010634670B2

(12) United States Patent
Cho

(10) Patent No.: US 10,634,670 B2
(45) Date of Patent: Apr. 28, 2020

(54) COMPOSITION COMPRISING OF A CONDUCTING POLYMER FOR DETECTING, CAPTURING, RELEASING, AND COLLECTING CELL

(71) Applicant: National Cancer Center, Goyang-si (KR)

(72) Inventor: Young-Nam Cho, Yongin-si (KR)

(73) Assignee: National Cancer Center, Goyang-si (KR)

( * ) Notice: Subject to any disclaimer, the term of this patent is extended or adjusted under 35 U.S.C. 154(b) by 231 days.

(21) Appl. No.: 14/141,366

(22) Filed: Dec. 26, 2013

(65) Prior Publication Data
US 2015/0147747 A1 May 28, 2015

(30) Foreign Application Priority Data

Nov. 25, 2013 (KR) .................. 10-2013-0143833

(51) Int. Cl.
*G01N 33/543* (2006.01)
*G01N 33/53* (2006.01)
*G01N 33/574* (2006.01)

(52) U.S. Cl.
CPC ..... *G01N 33/5308* (2013.01); *G01N 33/5438* (2013.01); *G01N 33/574* (2013.01)

(58) Field of Classification Search
CPC .................. G01N 33/48; G01N 33/5438
See application file for complete search history.

(56) References Cited

U.S. PATENT DOCUMENTS

2006/0035208 A1    2/2006  Roget et al.
2006/0207878 A1*   9/2006  Myung ............ G01N 33/5436
                                                 204/403.09
2010/0330706 A1   12/2010  Wei et al.

FOREIGN PATENT DOCUMENTS

KR   10-2000-0008880 A    2/2000
KR   10-2011-0101072 A    9/2011
KR   10-2013-0081952 A    7/2013
WO   WO-2012016136 A2 *  2/2012  ............ G01N 33/48

OTHER PUBLICATIONS

Cho et al., "Biotin-Doped Porous Polypyrrole Films for Electrically Controlled Nanoparticle Release", Langmuir, vo. 27, pp. 6316-6322, published Apr. 18, 2011.*

(Continued)

*Primary Examiner* — Tracy Vivlemore
*Assistant Examiner* — Nam P Nguyen
(74) *Attorney, Agent, or Firm* — Vorys, Sater, Seymour & Pease LLP; Mih Suhn Koh

(57) ABSTRACT

The present invention relates to a composition in which a conducting polymer is doped with a dopant, and a diagnostic apparatus, and more particularly, to a composition which is used to diagnose a disease and detect a biomaterial and also used for qualification and diagnosis by effectively and non-destructively collecting a captured biomaterial. Further, the composition can maximize capturing efficiency by being attached to a surface of a nano-structured scaffold and can be used as an ultrahigh-sensitive sensor using various linked bodies.

5 Claims, 15 Drawing Sheets

(56) References Cited

OTHER PUBLICATIONS

Persson et al.. ("Electronic Control of Cell Detachment Using a Self-Doped Conducting Polymer", Adv. Mater. vol. 23, pp. 4403-4408, published Aug. 23, 2011) (Year: 2011).*

Sekine et al., "Functionalized conducting polymer nanodots for enhanced cell capturing: the synergistic effect of capture agents and nanostructures," Advanced Materials, 23: 4788-4792, 2011.

Liu et al., "Hydrophobic Interaction-Mediated Capture and Release of Cancer Cells on Thermoresponsive Nanostructured Surfaces," Advanced Materials, www.wileyonline.com, published online Feb. 29, 2012.

Nagrath et al., "Isolation of rare circulating tumour cells in cancer patients by microchip technology," Nature, vol. 450: 1235-1240, Dec. 2007.

* cited by examiner

COMPOSITION COMPRISING OF A CONDUCTING POLYMER FOR DETECTING, CAPTURING, RELEASING, AND COLLECTING CELL

CROSS-REFERENCE TO RELATED APPLICATION

This application claims priority to and the benefit of Korean Patent Application No. 2013-0143833, filed on Nov. 25, 2013, the disclosure of which is incorporated herein by reference in its entirety.

FIELD OF THE INVENTION

The present invention relates to an apparatus capable of capturing and collecting a cell or the like from a biological sample and a method for isolating and collecting the same, and more particularly, to an apparatus and method of effectively capturing biomolecules, antigens, antibodies, cells, or the like in a conducting polymer and isolating nondestructively captured cells to be used for diagnosing a disease.

BACKGROUND OF THE INVENTION

Conducting polymers are polymers typically having a conductivity of $10^{-7}$ Scm$^{-1}$ (higher than that of semiconductors) or higher. In most cases, a high conductivity can be obtained by doping an electron acceptor or an electron donor into a polymer. Doped polyethylene, polypyrrole, and polythiopene are representative examples of conducting polymers.

Polyanilline, polypyroole, and polythiopene as conducting polymers have attracted a lot of attention since they can be easily polymerized and have relatively high electrical conductivities and excellent properties such as oxidation stability and the like. These high-molecular compounds exhibit a corrosion resistance and an electrochromic characteristic in addition to an electrical conductivity. Further, they have been widely applied to electronic devices such as semiconductors since they have merits of being light and easily processable as properties of polymers.

Polyacetylene is the first-discovered conducting polymer. It is just a semiconductor, but when processed with iodine, it has an electrical conductivity which is substantially equivalent to that of a metal. The research on conducting polymers has begun after the discovery of an insulator-metal phase transition phenomenon in which an electrical conductivity is sharply increased by doping halogen elements into polyacetylene and a $(CH)_x$ film. Since the polymer such as polyacetylene is comprised of a chain of carbon atoms with alternating single and double bonds between them, π-electrons can be somewhat freely moved. Thus, it is called a "π-conjugated polymer". Further, if such a polymer is chemically or electrochemically doped, its electrical conductivity can be regulated in a range of from a conductivity of an insulator to a conductivity of a metal. Thus, it is also called a "conducting polymer" or a "synthetic metal". The conducting polymers have been widely applied not only to the field of chemistry or physics but also to various industry fields due to their characteristics of being pliable and light like plastics.

A Circulating Tumor Cell (CTC) refers to a rare cancer cell that is present in the blood and circulates in the body and plays an important role in tumor metastasis. Therefore, detecting circulating tumor cells remains for a long time as an unsolved problem for diagnosing and treating a cancer.

According to the current anticancer treatments, most of patients are uniformly administered with anticancer drugs without checking presence or absence of such CTCs or DTCs (Disseminated Tumor Cells). It is necessary to selectively administer anticancer drugs depending on presence or absence of CTCs by detecting and analyzing the CTCs, or it is necessary to improve efficacy of drugs through personalized administration of drugs depending on molecular characteristics of CTCs.

Circulating tumor cells are known as a factor involved in cancer metastasis and cancer recurrence, and in particular, it is suggested that the circulating tumor cells are likely to include cancer stem cells which is one of the most important subjects of recent cancer research. Therefore, through analysis of circulating tumor cells, a possibility of new cancer prognosis prediction which cannot be obtained by traditional biopsies and a possibility of developing a patient-personalized treatment based it are expected.

However, such circulating tumor cells are very small in quantity within the blood and the cells are weak, and, thus, it is very difficult to detect and quantify them. Therefore, a highly sensitive diagnosis method capable of detecting circulating tumor cells, cancer cells, or cancer stem cells present in the body of a patient is still needed, and a method for efficiently isolating circulating tumor cells contained in a biological sample and an apparatus related thereto are still demanded.

In recent decades, significant efforts have been directed toward the development of novel strategies for acquiring, sorting, and characterizing desired pure cells from complex cell mixtures. Cell isolation and detailed analysis of purified cells is essential for research in a variety of fields such as fundamental biology and for the development of new clinical diagnostics and therapeutic modalities.

Isolation of rare cells such as cancer stem cells and circulating tumor cells (CTCs) from various sources is at great needs because rare types of cancer cells are critical for unraveling mechanisms that are associated with unrestricted cancer development and progression. In particular, because circulating tumor cells play an important role in the metastatic spread of cancer, detection of the circulating tumor cells could have an impact on establishing a theory of metastasis, which consequently introduces the possibility of point-of-care (POC).

Approaches that rely primarily on antigen-antibody affinity by recognizing biomarkers found on target cell membranes with high affinity and specificity have been developed. These include immune-magnetic beads, and micro- and nano-structured surfaces. Compared with traditional bench-top methods such as flow cytometers, the CellSearch system, isolation by size of epithelial tumor cells, current platform-based technologies have demonstrated improved cell recovery and purity and enhanced enrichment of target cells from blood samples.

However, although recent findings have typically focused on enhancing capture yield and sensitivity, techniques for demonstrating the feasibility of non-destructive release of captured cells and subsequent characterization of retrieval cells have not been actively developed.

PRIOR ART DOCUMENT

Patent Document

Korean Patent Laid-open Publication No. 10-2013-0081952

BRIEF SUMMARY OF THE INVENTION

An object of the present invention is to provide a method for detecting a pathogenic material by using a doped composition, wherein the doped composition consists of a dopant and a conducting polymer in order to provide a composition for isolating and collecting a biomaterial by using a conducting polymer.

Another object of the present invention is to provide a disease diagnostic apparatus comprising a doped composition, wherein the doped composition consists of a dopant and a conducting polymer.

Still another object of the present invention is to provide a method for acquiring a pathogenic material by using a doped composition, wherein the doped composition consists of a dopant doped into a conducting polymer.

In order to achieve the above objects, an exemplary embodiment of the present invention provides a method for detecting a pathogenic material by using a doped composition, wherein the doped composition consists of a dopant and a conducting polymer.

In an exemplary embodiment of the present invention, the dopant may be doped into the conducting polymer.

In an exemplary embodiment of the present invention, the composition may be doped with a dopant including one or more dopants selected from the group consisting of biotin, streptavidin, and antibody.

In an exemplary embodiment of the present invention, the antibody may be an anti-EpCAM (Epithelial Cell Adhesion Molecule), an anti-PSA (Prostate-Specific Antigen: KLK3 (Kallikrein)), an anti-PSMA (Prostate-Specific Membrane Antigen), an anti-PSCA (Prostate Stem Cell Antigen), an anti-STEAP (Six Transmembrane Epithelial Antigen of the Prostate), an anti-hTERT (human TElomerase Reverse Transcriptase), an anti-WT1 (Wilms tumor 1), an anti-MAGE (Melanoma Antigen Family A)-A2, an anti-5T4(oncofetal antigen 5T4), an anti-MAGE-A3, an anti-MUC1 (Mucin 1, cell surface associated), an anti-Her-2/neu (human epidermal growth factor receptor 2), an anti-CEA (Carcinoembryonic Antigen), an anti-survivin, an anti-MAGE-C1, or an anti-MAGE-C2.

In an exemplary embodiment of the present invention, the doped composition may have a form in which an antibody is bonded to a conducting polymer or a form in which an antibody is bonded to a linked body including biotin and streptavidin repeatedly linked in order.

In an exemplary embodiment of the present invention, the linked body repeatedly linked in order may include 1 to 50 singly linked bodies of biotin and streptavidin repeatedly linked.

In an exemplary embodiment of the present invention, the pathogenic material may be an antibody, a blood corpuscle, DNA, RNA, a protein, an enzyme, bacteria, a virus, or a cell.

In an exemplary embodiment of the present invention, the cell may be a cancer cell.

In an exemplary embodiment of the present invention, the cancer cell may be a liver cancer cell, a colorectal cancer cell, a rectal cancer cell, an endometrial cancer cell, an ovarian cancer cell, a renal-pelvis cancer cell, a pancreas cancer cell, a small intestine cancer cell, a hepatobiliary pancreas cancer cell, a stomach cancer cell, a brain tumor cell, a breast cancer cell, an MCF7 cell, a HeLa cell, or a CTC (Circulating Tumor Cell).

In an exemplary embodiment of the present invention, the conducting polymer may be polyacetylene, polypyrrole, polythiophene, poly-PEDOT (poly(3,4-ethylenedioxythiophene)), polyaniline, or a derivative thereof.

In an exemplary embodiment of the present invention, the composition may have a nanowire structure, a nanohair structure, or a nanopillar structure.

In an exemplary embodiment of the present invention, the composition may be attached onto a surface of gold (Au), platinum (Pt), silver (Ag), copper (Cu), iron (Fe), or ITO (Indium Tin Oxide).

In an exemplary embodiment of the present invention, the detecting may be measuring a change in an electric current.

Further, an exemplary embodiment of the present invention provides a disease diagnostic apparatus comprising a doped composition, wherein the doped composition consists of a dopant and a conducting polymer.

In an exemplary embodiment of the present invention, the disease diagnostic apparatus may be a biosensor.

Furthermore, an exemplary embodiment of the present invention provides a A method for acquiring a pathogenic material by using a composition, wherein the doped composition consists of a dopant doped into a conducting polymer.

In an exemplary embodiment of the present invention, the method may include changing a voltage, changing a current, or addition of a compound.

In an exemplary embodiment of the present invention, the compound may be glutathione.

A cell collecting apparatus comprising a conducting polymer according to the present invention can detect biomaterials even if a few biomaterials are present in a biological sample, can efficiently capture various biomaterials including circulating tumor cells, and can collect biomaterials without damage. Thus, it is useful for quantification and can be used for diagnosing and studying cancers or infectious diseases.

Further, if a biosensor having a nanostructure is used, capture and collection efficiency is very high. If it is applied to various devices for diagnosis, detection, and collection, a real-time checkup can be carried out.

DETAILED DESCRIPTION OF THE INVENTION

Figure 1:
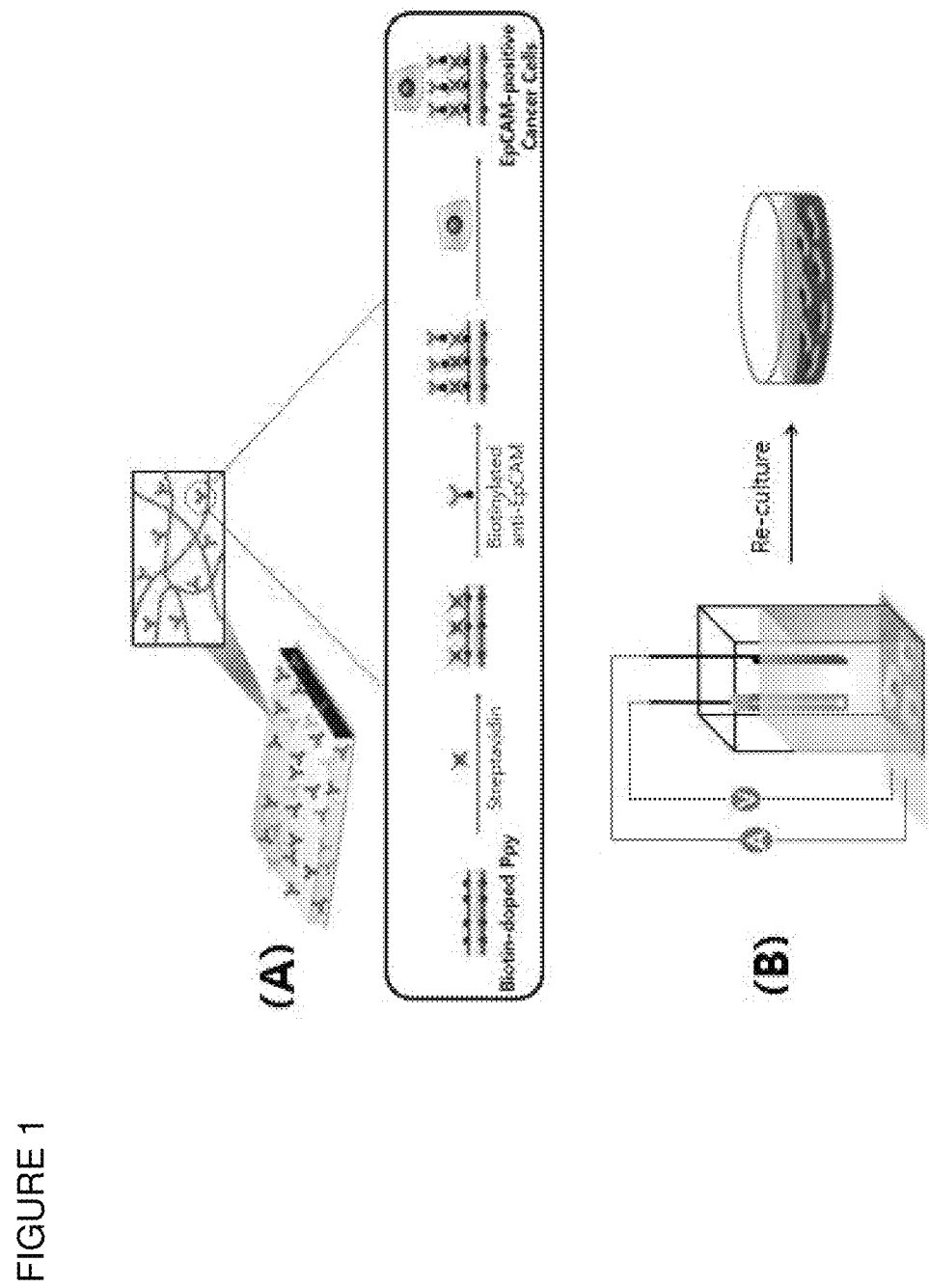
FIG. 1(A) illustrates a specific capture of epithelial cell adhesion molecules (EpCAMs) by an anti-EpCAM-immobilized, biotin-doped biotin-doped polypyrrole (Ppy) platform.
FIG. 1(B) illustrates that the captured cell is isolated without damage by electrical stimuli and is re-cultured.

The present invention first established the fact that a biomaterial as a target material present in a sample can be captured by doping an antibody or a linked body into a conducting polymer and the target material can be collected again without damage. Therefore, the present invention provides a composition for capturing, detecting, or collecting a biological material as a target material by using a conducting polymer and also provides an apparatus comprising the composition and a collecting method.

The present inventors researched, with interest, a biosensor for capturing or measuring a biological material for diagnosing a disease or the like and found that when cells captured by the biosensor was checked through a clinical method, it was very difficult to stably isolate the biological material without damage to the cells, which affected a test result. The present inventors completed the present invention based on this finding.

A conducting polymer repeatedly expands and contracts in response to a change in external electrical stimuli and thus can be used to start and stop loaded molecules at a required time. Although metals have been used for a long time as representative electrical stimulus responsive materials based on their excellent thermal conductivity and electrical conductivity, when transplanted into a living body, they cause sides effects such as stimuli to tissues and inflammations as a result of a restricted reaction caused by a wide difference in mechanical strength and a difficulty in surface modification. Meanwhile, conducting polymers have been used in various studies due to their merits of high processability, high electrical conductivity, excellent bioaffinity, environmental stability, and reversible volume change.

Among the conducting polymers, a polypyrrole film has excellent in vivo stability and easiness in preparation by electroplymerization, and, thus, it has been applied for various academic purposes or practical purposes such as a chemical/bio sensor, a supercapacitor, and the like.

However, the present invention is significant in the sense that the present invention first established the fact that during electropolymerization, wide difference in volume (about 35 vol %) of polypyrrole is made due to doping/de-doping mechanisms with respect to anions within a conducting polymer, and by using such a principle, an intelligent platform can be manufactured so as to detect and isolate a biological target material such as bacteria, a virus, a gene, a protein, a cell, or the like.

The terms used in the present invention are defined as follows.

Through the present specification, the term "comprises or includes" and/or "comprising or including" used in the document means that the described steps or materials are include but any other step or material are not excluded unless context requires otherwise.

The term "conducting polymer" means a polymer having electrical conductivity and can be obtained by electropolymerizing monomers.

The term "doping" used in the present invention is a term used in the polymer chemistry and means a method or a state in which a dopant as an additive is mixed (or introduced) into a polymer film. Further, the term "de-doping" means that dopants are released from polymer matrix.

The term "capturing" used in the present invention includes separating and gathering trace elements present in a certain material by various methods and means combination between a specific material and a target having a particularly high reactivity. The target may include various biomaterials such as a cell, an antigen, an antibody, a microorganism, etc.

All technical terms used in the present invention have the usual meaning conventionally understood by one of ordinary skill in the art to which this invention pertains, unless context defines otherwise. Further, although preferable methods and materials are described in the present specification, those similar or equivalent to the methods and materials fall within the scope of the present invention. All publications cited in the present specification as reference documents are incorporated herein by reference in their entirety.

The present invention is the first attempt to use a biotin-doped conducting polymer platform appropriate for specific capture and enrichment of epithelial-cell adhesion molecule antibody (anti-EpCAM)-positive cells and non-destructive, weak electrical potential-mediated release. Conducting polymers such as polypyrrole (Ppy) have widely been used in novel polymeric implants or even as drug carriers because they can harbor a variety of anions, cations, growth factors, anti-inflammatory drugs, ATP, and glutamate through simple electropolymerization. These dopants captured in a Ppy electrode film are specifically released when triggered by electric fields.

Figure 3:
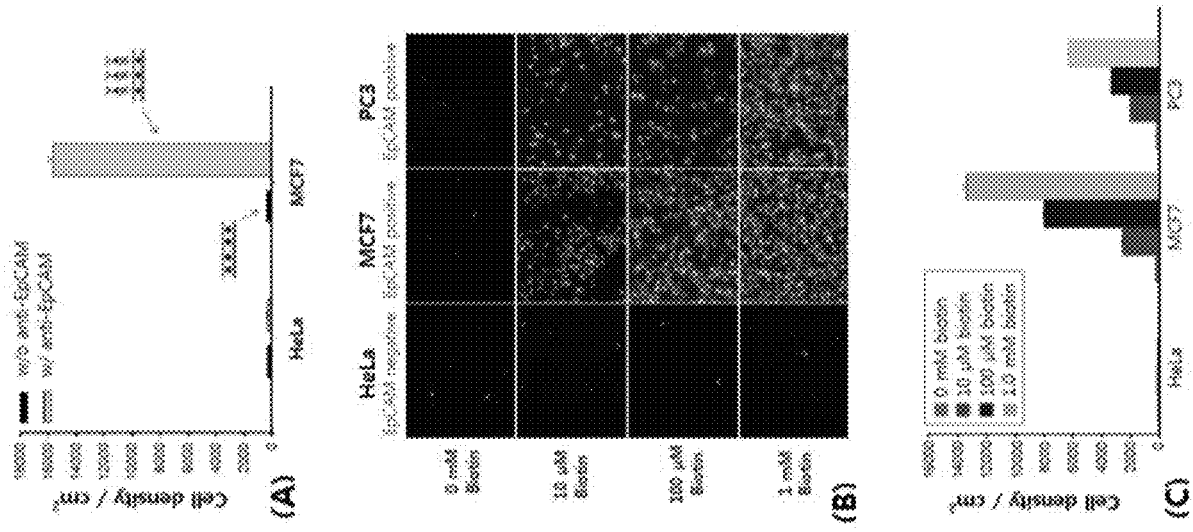
FIG. 3(A) shows evaluation of a cell-capture yield of an anti-EpCAM-immobilized, biotin-doped Ppy platform with or without an anti-EpCAM on EpCAM-negative cell (for example, HeLa or the like) and EpCAM-positive (for example, MCF7) cells.
FIG. 3(B) shows fluorescence images of HeLa, MCF7, and PC3 cells captured on the anti-EpCAM immobilized, biotin-doped Ppy platform depending on a biotin concentration.
FIG. 3(C) shows a quantitative analysis of various cells bonded to the anti-EpCAM immobilized to the biotin-doped Ppy platform surfaces labeled at different densities of biotin.

The present invention employs this technique to efficiently capture and release EpCAM-positive cancer cells. Biotin as a counteranion for Ppy formation can make high affinity interactions with targets through biotin-streptavidin coupling. FIG. 3C shows more details with regard to the number of cells bound depending on the amount of biotin incorporated within Ppy. With the increased concentration of biotin, the greater would be the buildup of EpCAM-positive cancer cells.

Considering that most surfaces are limited to inducing suitable functionalities with various biomolecules, doping of biotin residue into polypyrrole (Ppy) can provide strong bonding or tethering sites for sequential reactions. Such biotin-doped Ppy makes these surfaces compatible with a variety of conjugation strategies and also offers structural and functional stability of a Ppy platform with respect to external electrical stimuli through repetitive oxidation and reduction processes of Ppy. Further, the biotin-doped Ppy ultimately provides profound insights into "smart" drug delivery systems.

The present inventors established an efficient alternative for nondestructive isolation of captured cells and demonstrated "On-demand" release of captured cells related to a magnitude of an electric field, as shown in FIG. 1(B).

<Sample and Apparatus>

1. Biotin-Doped Polypyrrole (Ppy)

Human EpCAM/TROP-1 biotinylated antibody (Anti-EpCAM) was purchased from R&D Systems. Pyrrole, biotin, sodium dodecylbenzene sulfonate (NaDBS), potassium ferricyanide, 1-ethyl-3-(3-dimethylaminopropyl)carbodiimide (EDC), N-hydroxysuccinimide (NHS), and streptavidin were purchased from Aldrich. Bovine serum albumin (BSA) was obtained from Bovogen. Milli Q water (Millipore, USA) was used in the preparation of all solutions.

2. Antibody-Doped Polypyrrole

Nanoporous anodic aluminum oxide (AAO) was purchased from Whatman, and a gold (Au) plating solution (Orotemp® 24 RTU Rack) was purchased from Technic™. Further, sodium hydroxide, pyrrole, poly sodium 4-styrenesulfonate, potassium ferricyanide III, potassium chloride, Tween-20, ascorbic acid, L-glutathione, immunoglobulin G, and human AB serum were purchased from Sigma-Aldrich.

An anti-human prostate specific antigen (PSA), a monoclonal antibody, and a human PSA kit were purchased from Anogen. Bovine serum albumin was obtained from Bovogen. Milli Q water (Millipore, USA) was used in the preparation of distilled water.

3. Measuring Device

Electrochemical measurement was carried out by using a potentiostat/galvanostat (BioLogic SP-150) including a platinum wire counter electrode and an Ag/AgCl reference electrode, and electrochemical impedance spectra were measured in a frequency band of from 200 kHz to 10 mHz at a formal potential of 200 mV and 5 mA.

The morphology of conducting polypyrrole nanowires was scanned with a field emission scanning electron microscope (FESEM: JEOL JSM-6701F).

Example 1

Biotin-Doped Polypyrrole (Ppy)

A Ppy film was prepared by using a 3-electrode system, and as a preparation apparatus, a potentiostat/galvanostat (BioLogic SP-150) was used. The apparatus was operated at room temperature, and a platinum wire was used as a counter electrode and Ag/AgCl was used as a reference electrode. A clean ITO (Indium Tin Oxide) was used as a working electrode for electropolymerization of polypyrrole.

Polymerization was carried out by using 0.1 M pyrrole and 0.01 M sodium dodecylbenzene sulfonate (NaDBS) aqueous solution containing various concentrations (1 mM, 0.1 mM, and 0.01 mM) of biotin using chronoamperometry (CA) at 0.8 V to 1.1 V (versus Ag/AgCl) for 2 seconds to 2 minutes. Thereafter, a biotin-doped Ppy film was deposited on a surface of the ITO and washed with ultrapure water 3 times and then dried.

Example 2

Antibody-Doped Polypyrrole

In an example of the present invention, antibody-doped polypyrrole can be used as a label-free biosensor capable of directly capturing or analyzing a target protein or antigen without additional linker or marker.

The present inventors prepared a film by mixing an anti-PSA (anti-Prostate Specific antigen) into a pyrrole solution so as to be used to detect a biomaterial by directly doping the antibody into the conducting polymer, and carried out electropolymerization of polypyrrole on surfaces of gold nanowires (Au NWs) (refer to FIG. 9(A)).

After a surface of the polypyrrole was blocked by BSA, a label-free electrochemical immunosensor was used.

A thin gold (Au) film having a thickness of 150 nm was thermally evaporated to be deposited on one side surface of an AAO (Anodic Aluminum Oxide) template serving as a working electrode. For electrochemical deposition, the AAO film, on which the gold was deposited, was positioned on a surface of conductive ITO (Indium Tin Oxide) of 1.5×2 cm² and then inserted into a commercial Teflon electroplating cell including an exposed open pore.

In order to form gold (Au) nanowires within the film, a commercial gold plating solution was poured into the Teflon cell, and electrodeposition was carried out at room temperature by scanning 100 times at a scan rate of 100 mV/s with an electrical potential in a range of −1.1 to 0 V by a cyclic voltammetry method.

The AAO template was manufactured by attaching carbon paste onto a gold (Au) surface and dried at 60° C. overnight.

This structure maintained a strong supporting structure when isolated gold (Au) nanowires remained.

The AAO template was dissolved in 2 M NaOH aqueous solution for 4 hours, and a fixed substrate was washed with distilled water several times. In order to dope the anti-PSA into a polypyrrole film, 10 μL (1 mg/mL) of the antibody was mixed with 0.01 M pyrrole and a PSS aqueous solution to make a total volume of 400 μL.

The polypyrrole was electrochemically deposited on the isolated gold (Au) nanowires. At that time, +0.8 V (Ag/AgCl) was applied for 20 seconds and the anti-PSA-doped conducing polypyrrole nanowires were washed with 1 wt. % Tween-20 (in 1×PBS) solution several times and then processed with 1 wt. % BSA (in 1×PBS) to block non-specific binding of the antigen. 1 hour later, the resultant polypyrrole nanowires were washed with 1 wt. % Tween-20 several times.

Example 3

Nanowire-Shaped Conducting Polymer Film

A conducting polymer film of the present invention can be used in a three-dimensional detecting or collecting apparatus.

Figure 8:
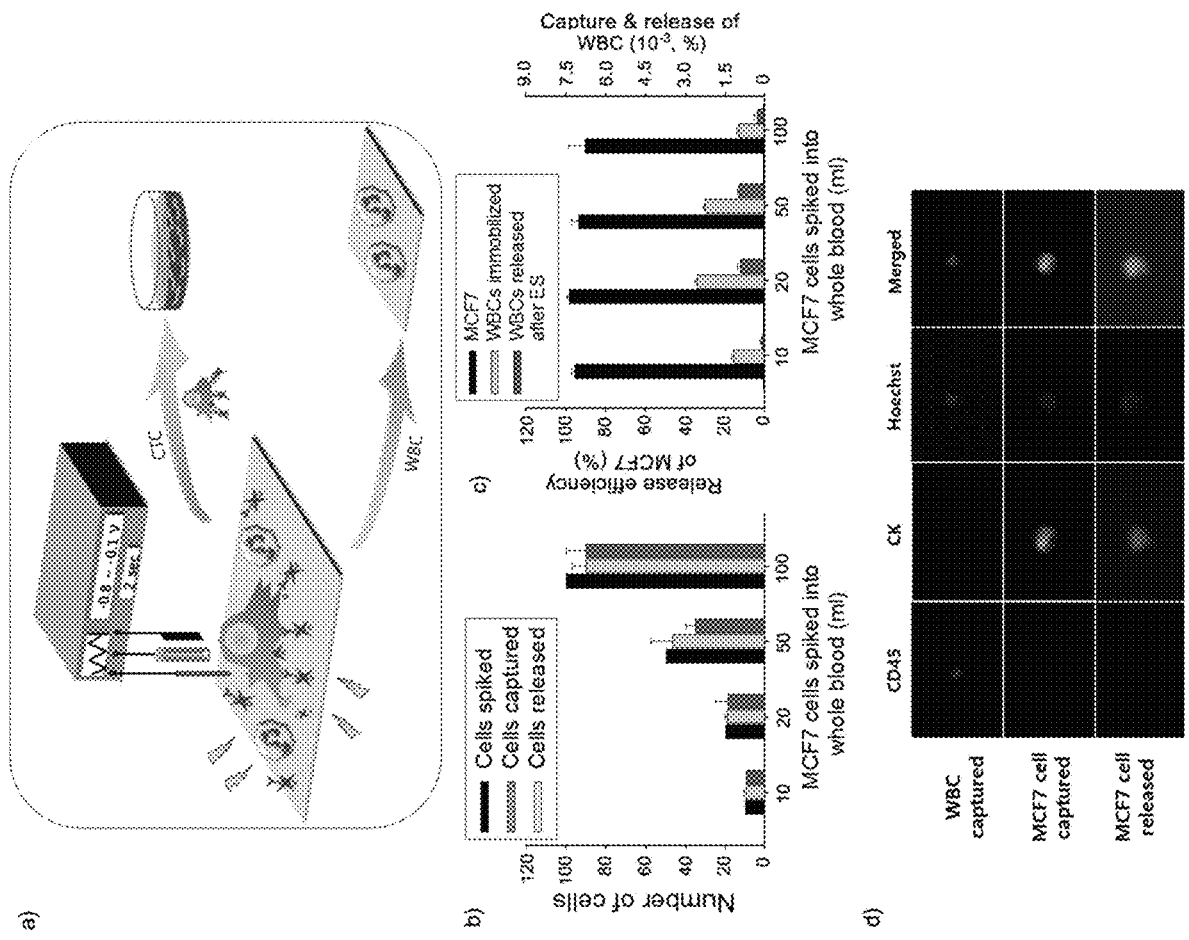
FIG. 8(A) shows an experiment carried out by artificially adding MCF7 cells to whole blood to check whether or not circulating tumor cells can be actually detected.
FIG. 8(B) is a graph showing that when 10 to 100 MCF7 cells mixed with blood were dropped to an anti-EpCAM immobilized polypyrrole film, most of the MCF7 cells were attached to a surface of the polypyrrole film.
FIG. 8(C) shows that 90% of the MCF7 cells could be collected without damage by electrical stimulation for 2 seconds, whereas most of blood cells were not attached to the surface of the polypyrrole film and, when applied with electrical stimulation, they were not released but remained on the surface of the polypyrrole film, and FIG. 8(D) provides images showing presence of CD45 specifically expressed in white blood cells and CK expressed in MCF7 cells as a result of immunofluorescence on the MCF7 cells and white blood cells captured by and released from the surface of the polypyrrole film.

After a scaffold was manufactured in the form of a nanowire or a nanopillar by using ITO or gold, a structure as shown in FIG. 8 was prepared by using the scaffold as a working electrode. When the structure was used for detection, a surface area per volume was maximized, which made it possible to capture more target materials. In the case of a target material having a large volume, the structure could be firmer due to a fine absorption effect. Further, by repeatedly bonding linkers 30 times or more, a nanowire structure could be manufactured. When used together with the scaffold structure, a surface area could be maximized.

The present inventors coated the AAO (Anodic Aluminum Oxide) template with gold and mixed 0.1 M polypyrrole with 0.01 M PSS and 1 mM NHS-SS-biotin solution to perform coating at 0.7 to 1.1 V by electropolymerization. Then, the AAO template was dissolved in 3 M NaOH, and only Ppy nanowires remained. Depending on an electropolymerization time, nanowires having various lengths (100 nm to 40 μm) could be obtained.

In this case, it was observed that the applied voltage affected a surface roughness of the nanowire structure, and a pore diameter of the AAO template used affected a diameter of the conducting polypyrrole nanowire structure.

Example 4

Cell Collection by Electrical Stimulation

Figure 2:
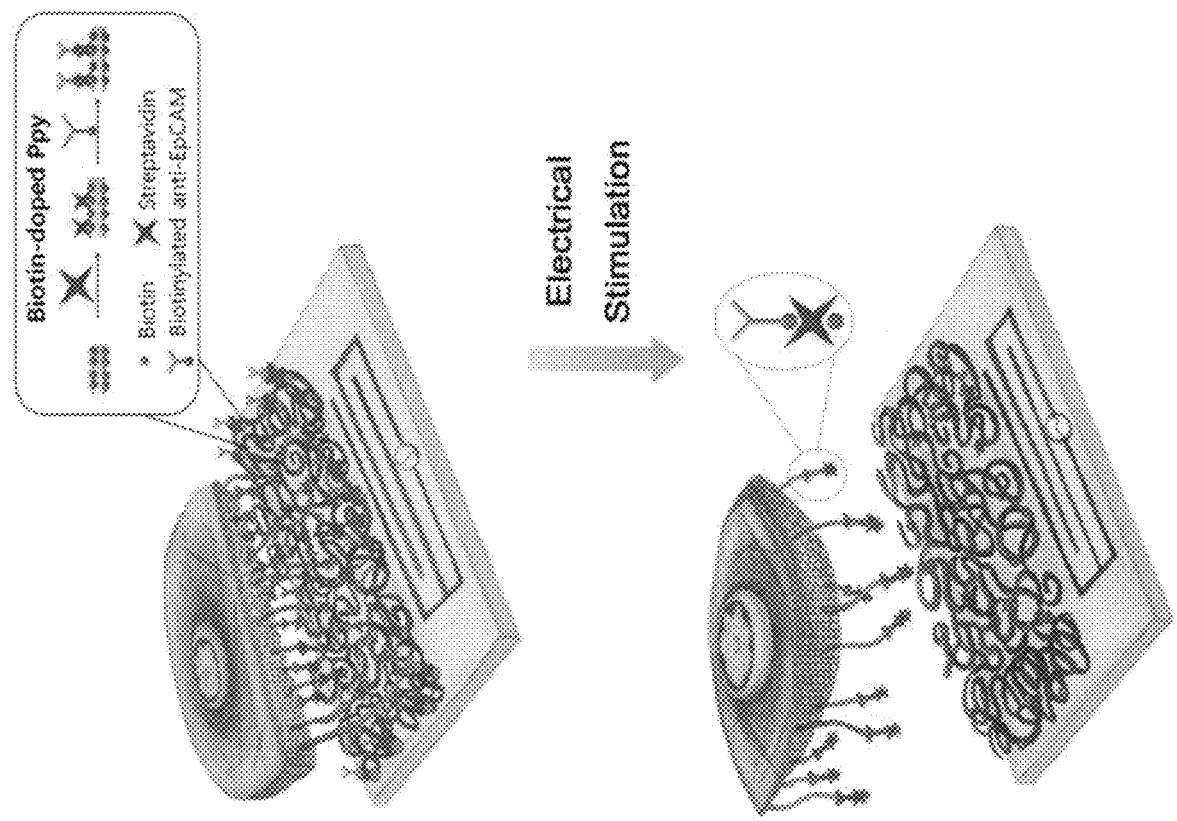
FIG. 2 illustrates that after an EpCAM expressing cell is effectively detected from a conducting polymer, when a negative DC electric field is applied, a polypyrrole polymer is expanded and a doped biotin molecule is naturally separated from the polymer and the captured cell is isolated.

The present invention can be used for diagnosis and analysis by non-destructively obtaining a biomaterial such as a cell bonded to a platform. By using a spontaneous redox behavior of a conducting polymer as a mechanism of action, an interaction between captured cells and biotin doped into polypyrrole can be regulated with a weak electrical potential, and, thus, it is possible to efficiently control bonding (refer to FIG. 2).

In order to isolate a biomaterial captured by a polypyrrole film, the present inventors used a 3-electrode system of a potentiostat/galvanostat (BioLogic SP-150) to collect the captured biomaterial (target). In order to check whether the biomaterial is efficiently and non-destructively collected or not, a collection yield, and survivability after collection, the present inventors conducted an experiment as follows.

1. Pre-Treatment

In order to check a method for non-destructively releasing captured cancer cells from anti-EpCAM-immobilized, biotin-doped polypyrrole, before the experiment, $2 \times 10^5$/mL of MCF7 cells were captured on a surface of the polypyrrole doped with 1 mM biotin, and unbonded or non-specifically bonded cells were removed by repetitive washing.

2. Collection Effect Depending on Electrical Potential

The present inventors applied a variety of electrical potentials to MCF7 cells on Ppy surfaces to investigate an effect of the electrical fields on cells.

After electric stimulation at a voltage of +0.8 V, +0.4 V, 0 V, −0.5 V, and −1.0 V for 2 to 15 seconds, the immobilized cells were incubated at 37° C. in 5% $CO_2$ for 30 minutes and permitted controlled release of the captured cells with gentle agitation in phosphate-buffered saline (PBS). Then, the immobilized cells were washed and stained with a cell marker.

Consistently showing programmable release of gold nanoparticles from biotin-doped Ppy films, preferential cell isolation and release was observed only when a negative electrical potential is applied to the film surfaces. As a result, a release pattern showed no sensitivity to those of positively stimulated Ppy surfaces; resulting in similarity to the control with no stimulation.

Figure 4:
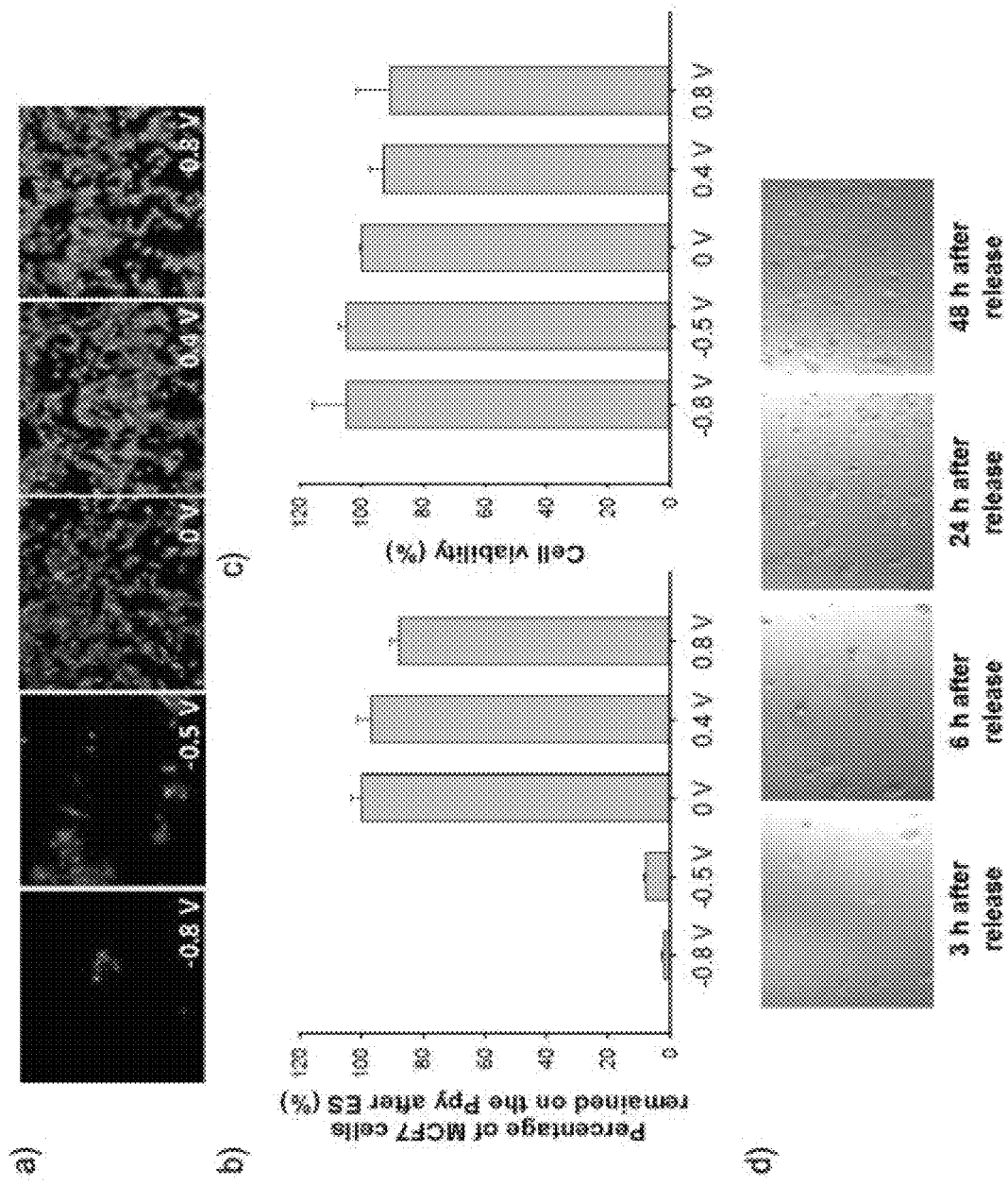
FIG. 4(A) shows release profiles of MCF7 cells captured on the anti-EpCAM immobilized, biotin-doped Ppy platform exposed to applied electric fields of +0.8 V, +0.4 V, 0 V, −0.5 V, and −0.8 V for 15 seconds.
FIG. 4(B) shows quantitation of the percentage of MCF7 cells remaining on the Ppy platform surfaces at the time of 30 minutes after application of an electric field for 15 seconds.
FIG. 4(C) shows viability of MCF7 cells collected from the Ppy platform surfaces after exposure to various electrical potentials for 15 seconds, and FIG. 4(D) provides optical microscope images showing time-dependent spread and proliferation of the cells released after electrical stimulation at −0.8 V for 15 seconds.

As can be seen from FIG. 4(B), only 15% of the cells remained on the surfaces after exposure to −0.5 V, and most of the cells were released from the Ppy surfaces after electrical stimulation with −0.8 V. During electropolymerization, wide difference in volume (about 35 vol %) of polypyrrole was made due to doping/de-doping mechanisms with respect to anions within a conducting polymer, and by using such a principle, the dopant doped into the polypyrrole were isolated and the captured cells were isolated.

To be specific, the major factors affecting the release of captured cells were associated with a reversible volume change, and to be more specific, the major factors affecting the release of captured cells were associated with a reversible volume change occurring as a result of an electrochemical reaction in conducting polymer chains during reduction-oxidation cycles. Such a reversible volume change occurred as a result of an electrochemical reaction in conducting polymer chains during reduction-oxidation cycles.

According to the experimental result, the repetitive reduced and oxidized state caused a large volume change, up to 35%, in response to an applied voltage. This process accounted for the release of large numbers of captured cells at negative potentials by altering a chemical strength of the interaction between Ppy and biotin.

3. Collection Effect Depending on Addition of Compound

In an example of the present invention, when a reducing agent such as glutathione was added, a binding affinity between biotin-doped Ppy and streptavidin-tagged cell complexes could vary and could arise due to an oxidation-reduction state of an engineered surface and a change in charge.

The present inventors coated an AAO (Anodic Aluminum Oxide) template with gold and mixed 0.1 M polypyrrole with 0.01 M PSS and 1 mM NHS-SS-biotin solution to perform electropolymerization, resulting in preparation of Ppy nanowires. Then, the AAO template was dissolved in NaOH to manufacture NHS-SS-biotin-dope Ppy nanowires.

Herein, the glutathione as a reducing agent cleaved a disulfide bond, i.e. SS (disulfide bond) site of the NHS-SS-biotin. Therefore, cancer cells bonded to the biotin could be isolated without damage.

Experimental Example 1

1. Cell Culture

MCF7 (breast cancer, EpCAM-positive), PC3 (prostate cancer, EpCAM-positive) and HeLa (cervical cancer, EpCAM-negative) cells were obtained from the American Type Culture Collection (ATCC) and cultured in Roswell Park Memorial Institute (RPMI)-1640 and Dulbecco's modified Eagle's medium (DMEM) supplemented with 5% fetal bovine serum (FBS; GenDepot).

2. Biotin-Doped Ppy Film Capturing Cells

A biotin-doped Ppy film on ITO was incubated in a solution containing EDC (0.095 g)/NHS (0.061 g) for 45 minutes, followed by washing with ultrapure water 3 times.

To immobilize the biotin-doped Ppy film, 50 mL of streptavidin (20 mg/mL in water) was placed on the film for 1 hour. The film was then washed with distilled water 3 times.

Thereafter, to bond an antibody to the streptavidin, the film was exposed to 30 mL of anti-EpCAM (10 mg/mL in 1×PBS solution) at 4° C. overnight and then washed with PBS. Then, 100 mL of 1 wt. % BSA (in 1×PBS) was added to the film surface to block non-specific bonding of an antigen.

After 1 hour, the film surface was washed with PBS several times and the ITO bonded to the Ppy film/streptavidin/anti-EpCAM was placed in a 12-well culture plate for cell attachment. To examine an adherence preference to the film surface, EpCAM-positive (MCF7, PC3) and EpCAM-negative (HeLa) cells were seeded at a density of $2 \times 10^5$ cells for 20 minutes. The resultant film was washed with PBS 3 times.

3. Western Blot

HeLa, MCF7, and PC3 cells were collected and lysed in a radio immunoprecipitation assay buffer solution, and protein samples (20 mg) were then separated on a 10% SDS-polyacrylamide gel and transferred to nitrocellulose filters.

The filters were blocked with 5% nonfat dry milk and an antibody against glyceraldehyde-3-phosphate dehydrogenase (GAPDH; Santa Cruz Biotechnology) was used as an internal regulator. Further, positive reactions were visualized by using a chemiluminescence detection system (Amersham Pharmacia).

4. Viability and Vitality Measurement of Collected Cells

The present invention can be used in an apparatus capable of collecting detected or captured materials without damage by using a polypyrrole film prepared by the above-described method. In order to collect cells captured by a biotin-doped polypyrrole film, the present inventors used a 3-electrode system of a potentiostat/galvanostat (BioLogic SP-150) and applied a voltage of −0.8 V, −0.4 V, +0.4 V, and +0.8 V for 2 to 15 seconds to the film surface to which the cells were attached.

In order to measure viability of cells, an experiment was conducted as follows. MCF7, PC3, and HeLa cells were seeded at a density of $2 \times 10^5$ cells on the Ppy film/streptavidin/anti-EpCAM for 20 minutes. The resultant film was washed with PBS 3 times. For staining, calcein AM (green, live) and ethidium homodimer-1 (red, dead) were added to a cell-laden film surface for 20 minutes. Further, labeled cells were examined under a fluorescence microscope (Zeiss LSM 710 ConfoCor 3).

In order to measure vitality of cells, an experiment was conducted as follows. Cell viability was determined by assaying surfaces of viable cells with a methylthiazole tetrazolium cell count kit-8 (Dojindo Molecular Technologies). After electrical stimulation, MCF7 cells were cultured to a density of $3 \times 10^4$ cells in 96-well plates.

After 24 hours, absorbance was measured at 540 nm by using a spectrophotometer (Molecular Devices, Emax).

5. Immunofluorescence

Cells were transferred to a coverslip plate and fixed and permeabilized as described above. Then, antibodies against EpCAM were applied to the coverslip plate, which was followed by incubation for 2 hours.

Thereafter, a secondary antibody conjugated with Alexa Fluor 488 (Invitrogen; green signal for EpCAM) was added, and the coverslip was incubated for 30 minutes.

DNA (blue signal) was stained with 1 mg/mL Hoechst 33258 (Invitrogen). Labeled cells were examined under a Zeiss LSM 710 fluorescence microscope.

Experimental Example 2

In order to check a preferential bond of anti-EpCAM to a conducting polymer platform of the present invention manufactured by the above-described method, the present inventors conducted an experiment as follows.

EpCAM-positive cells such as MCF7 breast cancer cells and PC3 prostate cancer cells and EpCAM-negative cells such as HeLa cervical cancer cells were processed at $2 \times 10^5$ cells/mL, and whether or not adsorption is made and an adsorption density were checked by means of immunofluorescence.

As shown in FIG. 3(A), no relationship was apparent between anti-EpCAM bonded to a Ppy substrate and HeLa cells. Meanwhile, MCF7 cells appeared to be strongly correlated with existence of anti-EpCAM.

In order to clarify an effect of cell density on a concentration of biotin doped into polypyrrole, an experiment as shown in FIGS. 3(B) and 3(C) was conducted. The concentration of biotin in the polypyrrole was correlated with the concentration of biotin applied without a big difference in capturing efficiency. Further, the obtained MCF7 and PC3 cell density was linearly proportional to the amount of biotin bonded to Ppy.

High density of biotin receptors leads to an increase in number of bonding sites for EpCAM-positive cells, resulting in an increase in adsorption of anti-EpCAM. FIG. 3(C) shows the number of cells bonded depending on the amount of biotin immobilized within Ppy. It was confirmed that with the increased concentration of biotin, the number of EpCAM-positive cancer cells was increased.

Experimental Example 3

The present inventors conducted an experiment as follows to check whether a collecting method of the present invention is an efficient and non-destructive method.

1. Viability of Collected Cells

Cyclic voltammetry as a representative example of voltammetry is an electrochemical assay method that is basically and mainly used to study electrochemical behaviors of redox species and a mechanism of oxidation-reduction reaction. A cyclic voltammetric curve can be obtained by circulating an electrical potential of a working electrode and measuring a current.

To test viability of released cells, the cells were collected and cultured again. As can be seen from FIG. 4(C), the experimental result showed that when weak electric fields ranging from (−) 0.8 V to 0.8 V were applied, cell viability was maintained at 90% or higher in all of the experiments and they did not affect cell viability. The collected cells were successfully cultured for more than 5 passages (3 days per passage). Based on this fact, it was confirmed that the biotin-doped Ppy platform can be most promising as an active cell capture/release platform.

Further, as can be seen from FIG. 4(D), the optical microscopic images give more details on the morphological changes of the released cells as a function of time after plating on a Petri dish. Soon after electrical stimulation, cells display more round or flattened appearance. However, the cells returned to their original form overall at the time of 24 hours after isolation, and most of the cells had a complete form at the time 48 hours after isolation. Morphologically, the cells progressively spread with time, returning to their original form and fully viable biological function.

2. Electrochemical Characteristics of Polypyrrole Film

In order to analyze electrochemical characteristics of biotin-doped Ppy films, it is essential to evaluate an electron-transfer capability of electroactive ferricyanide species throughout Ppy surfaces. Thus, the present inventors conducted an experiment as follows.

By using 5 mM ferricyanide probe solution as an indicator, electrical stimulation was applied, and then Cyclic voltammetric (CV) curves were drawn to measure effects thereof.

Figure 5:
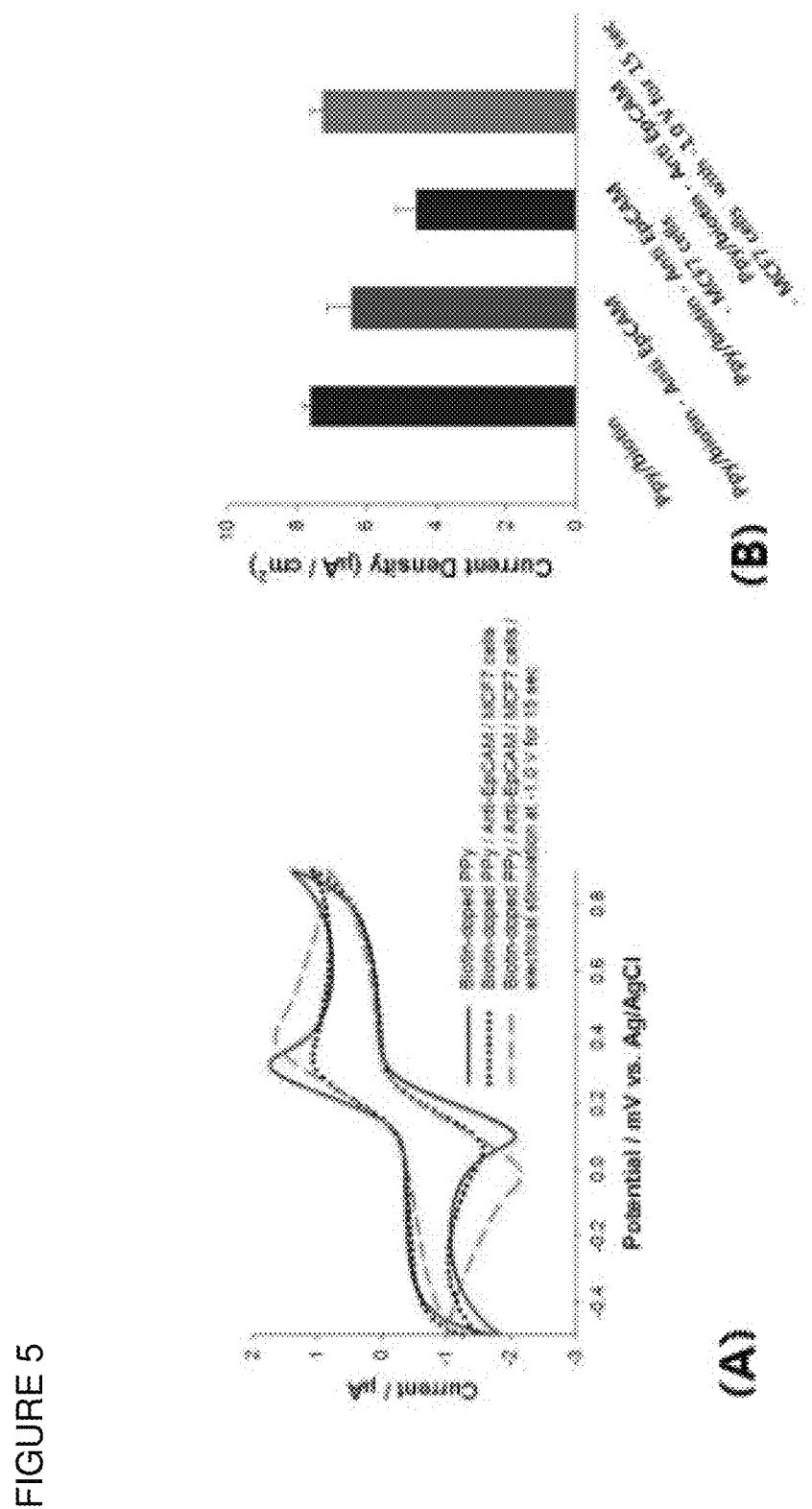
FIG. 5(A) provides Cyclic voltammetric (CV) curves to show effects thereof.
FIG. 5(B) shows an average current density obtained from ferricyanide CV on various surfaces.

As can be seen from FIG. 5(A), according to the experimental result, the biotin-doped Ppy surfaces showed obvious peak potentials for oxidation and reduction current, whereas the biotin-doped Ppy surfaces showed significant changes in redox peaks.

This behavior is most likely caused by the immobilization of anti-EpCAM and MCF7 cells on the Ppy surfaces, which readily blocks free transfer of electrolytes.

Further, FIG. 5(B) shows an average current density obtained from ferricyanide CV on various surfaces, and each point represents the mean plus or minus standard deviation of 3 separate experiments. 5 mM $Fe(CN)_6^{3-/4-}$ was used for measurement.

A blue bar represents biotin-doped Ppy, and a red bar represents anti-EpCAM immobilized, biotin-doped Ppy surfaces. A black bar represents captured MCF7 cells on anti-EpCAM immobilized, biotin-doped Ppy surfaces, and a green bar represents Ppy surfaces after electrical stimulation at −0.8 V for 15 seconds (green) at a scan rate of 100 mV/sec. The electric-field-mediated desorption of biomolecules and MCF7 cells resulted in a dramatic increase in a magnitude of a redox current.

The application of electrical stimulation of −0.8 V for 15 seconds was sufficient to restore the peak intensity by removing the biomolecular assemblies from the Ppy surfaces. FIG. 5(B) shows the maximum peak currents obtained by cyclic voltammetry conducted by using ferricyanide solutions as sensitive redox indicators. This shows that such electrochemical responses were direct evidence of the adsorption and desorption process of the anti-EpCAM/MCF7 cells from the Ppy surfaces.

3. Expression Profile of Released Cells

To obtain a molecular expression profile of released cells, the present inventors used electric-field-mediated approaches and evaluated an expression degree of an EpCAM antigen expression by conducting immunofluorescence and quantification with a Fujifilm Multigauge 3.0. In this case, when cells were isolated, an applied electric field should be chosen to untangle the biotin-Ppy bond without causing damage to the cell structure and biological functions thereof. To measure electric potential effects on loss of EpCAM levels in HeLa and MCF7 cells, the present inventors conducted a Western blot analysis, carried out electrical stimulation at −0.8 V for 15 seconds, and detected EpCAM expression in MCF7 cells. The cells were stained by using an anti-mouse immunoglobulin G secondary antibody (green) and counterstained with Hoechst 33342 (blue) and glyceraldehyde-3-phosphate dehydrogenase (GAPDH). Western blotting results after electrical stimulation were summarized in a histogram in which the protein expression was calculated using a Fujifilm Multigauge 3.0.

Figure 6:
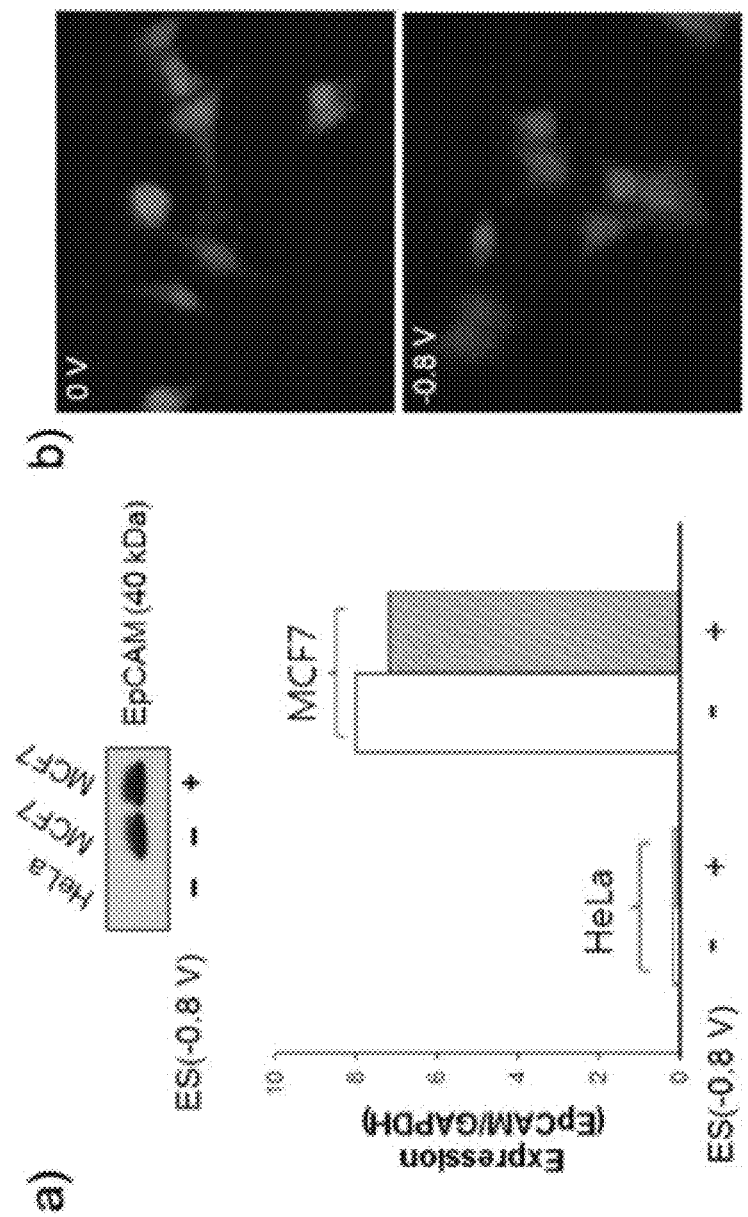
FIG. 6(A) shows results of Western blot analysis on EpCAM protein expression (upper part) and Western blotting results of electrical stimulation carried out at −0.8 V for 15 seconds.
FIG. 6(B) shows detection of EpCAM expression in MCF7 cells depending on absence or presence of an electric field at −0.8 V for 15 seconds.

According to the experimental result, as shown in FIG. 6(A) and FIG. 6(B), a negligible effect on the EpCAM protein band in MCF7 cells was observed even when using a negative potential of −0.8 V. Similar to results in the control cells (0 V), the EpCAM protein was abundantly expressed in green and mostly localized in the cytoplasm and membrane of the released cells.

4. Specific Capture of Anti-EpCAM

To demonstrate specific recognition of EpCAM-positive cells by the biotin-doped Ppy platform, the present inventors conducted a comparative experiment between a mixture sample of MCF7 cells ($2\times10^5$ cells/mL) and HeLa cells ($2\times10^5$ cells/mL) at a mixture ratio of 1:1 and a mixture sample of MCF7 cells ($2\times10^5$ cells/mL) only.

Figure 7:
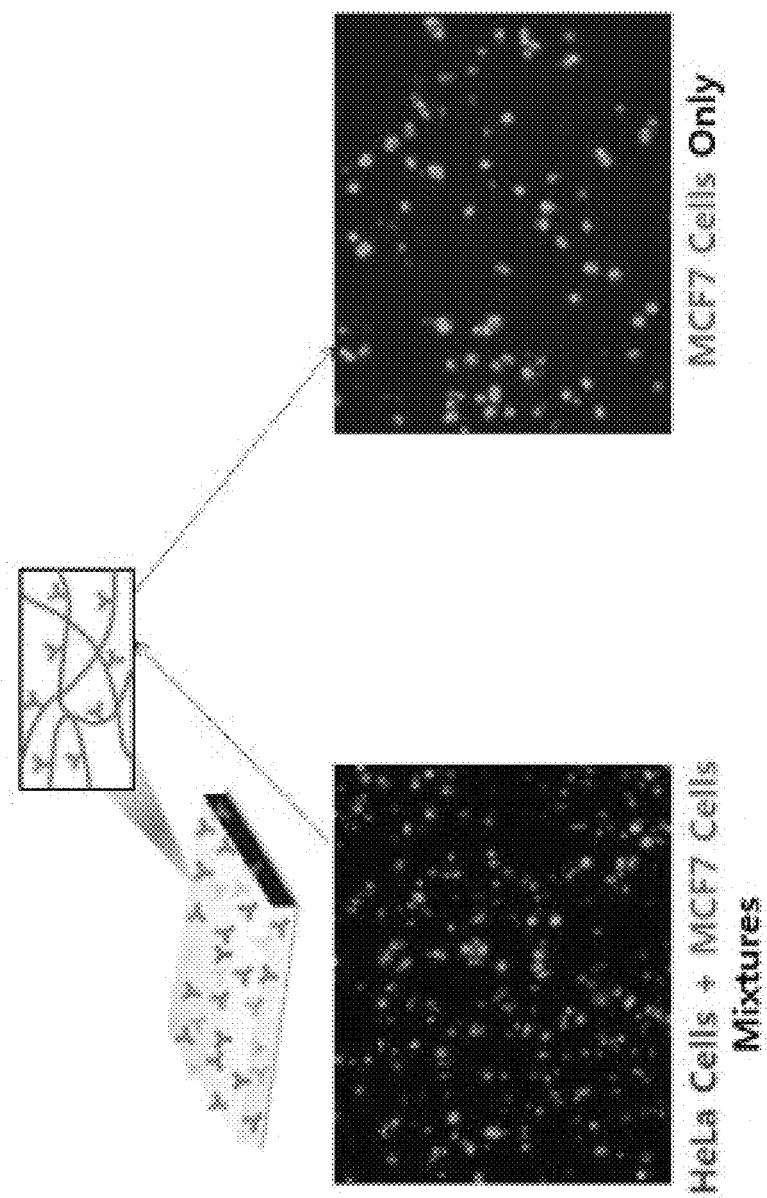
FIG. 7 shows a result of specific capture of EpCAM-positive MCF7 cells from a mixture of cells using anti-EpCAM immobilized, biotin-doped Ppy.

According to the experimental result, as shown in FIG. 7, in the experiment of specific capture of EpCAM-positive MCF7 cells from the mixture of cells by using anti-EpCAM immobilized, biotin-doped Ppy, the biotin-doped Ppy surfaces revealed 95% of fluorescent green (MCF7 cells) excluding any red HeLa cells, which confirmed the specific capture. From this result, it could be seen that the present invention captured cells with efficiency of 93% and purity of 95%. Further, from this result, it is deemed that the present invention can be a valuable tool for cell capture and non-destructive cell collection with high efficiency and purity.

Experimental Example 4

The present inventors manufactured a Ppy film by adding anti-PSA to gold nanowires (Au NWs) and blocked the film by BSA. Then, the present inventors dropped 1 ng of PSA thereto and monitored a change in current by using Differential Pulse Voltammetric Determination (DPV).

Further, in order to measure a change in current depending on a change in amount of the BSA, after the anti-PSA was added to the gold nanowires (Au NWs) and blocked by the BSA, a current capacity was measured at various amounts of from 100 fg to 10 ng of the PSA.

Figure 9:
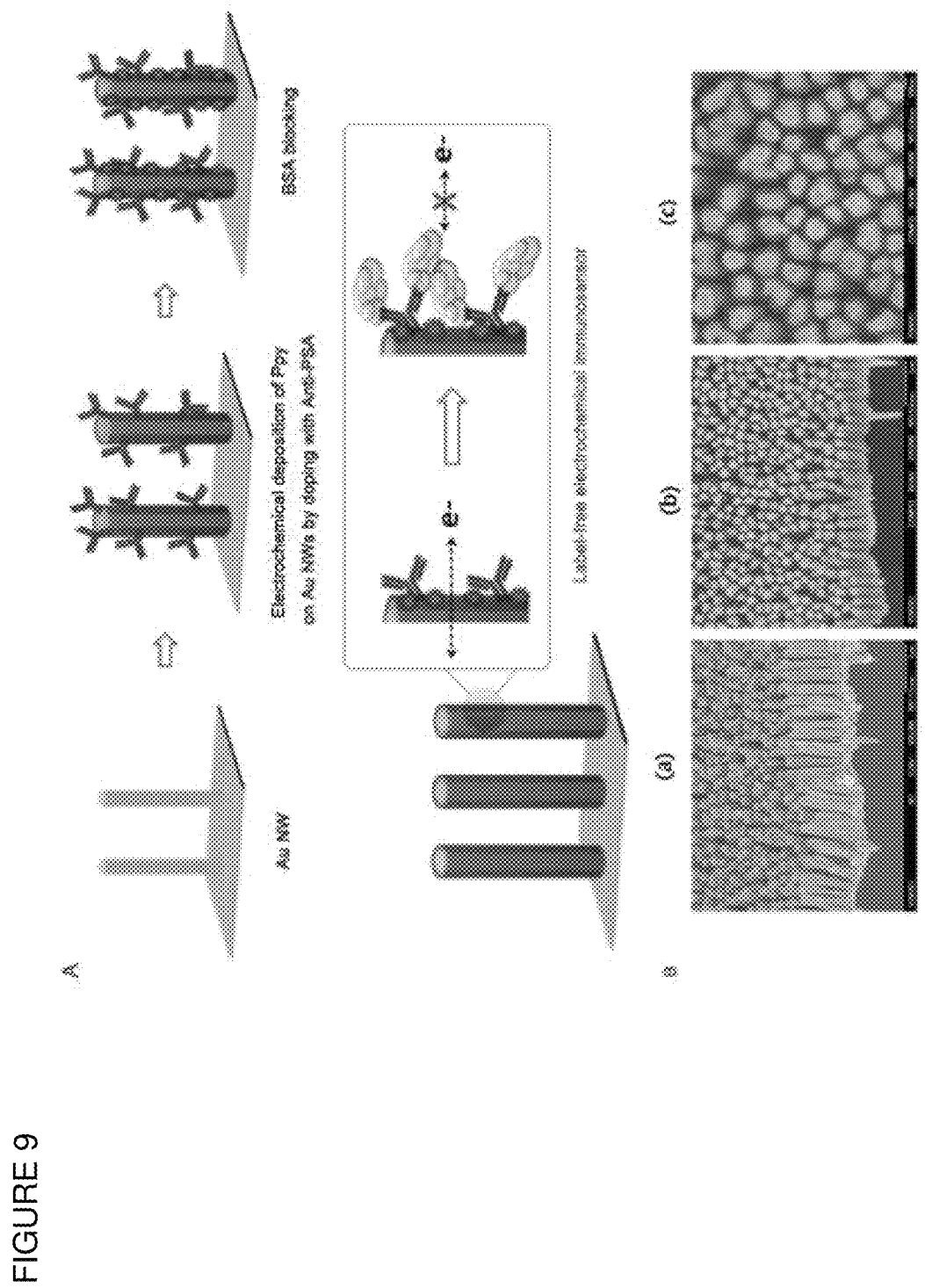
FIG. 9(A) shows a change in current depending on a concentration of an anti-PSA (Anti-Prostate Specific Antigen) after polypyrrole doped with the anti-PSA is coated on surfaces of gold nanowires (Au NWs) by electropolymerization and blocked by BSA, and FIG. 9 (B) provides electron microscope images of the gold nanowires (Au NWs) (a) and gold nanowires coated with an anti-PSA-doped polypyrrole film (b and c)

As shown in FIG. 9, a peak value appeared at a voltage between 0.1 V to 0.3 V. When the film surface was blocked by the PSA with the anti-PSA, a current value was the lowest at 25 μA. When only the gold nanowires were used, a current value was the highest at 62 μA.

From this result, it could be seen that more materials captured by the gold nanowire surfaces made electrons difficult to pass through and a current value was decreased.

Figure 10:
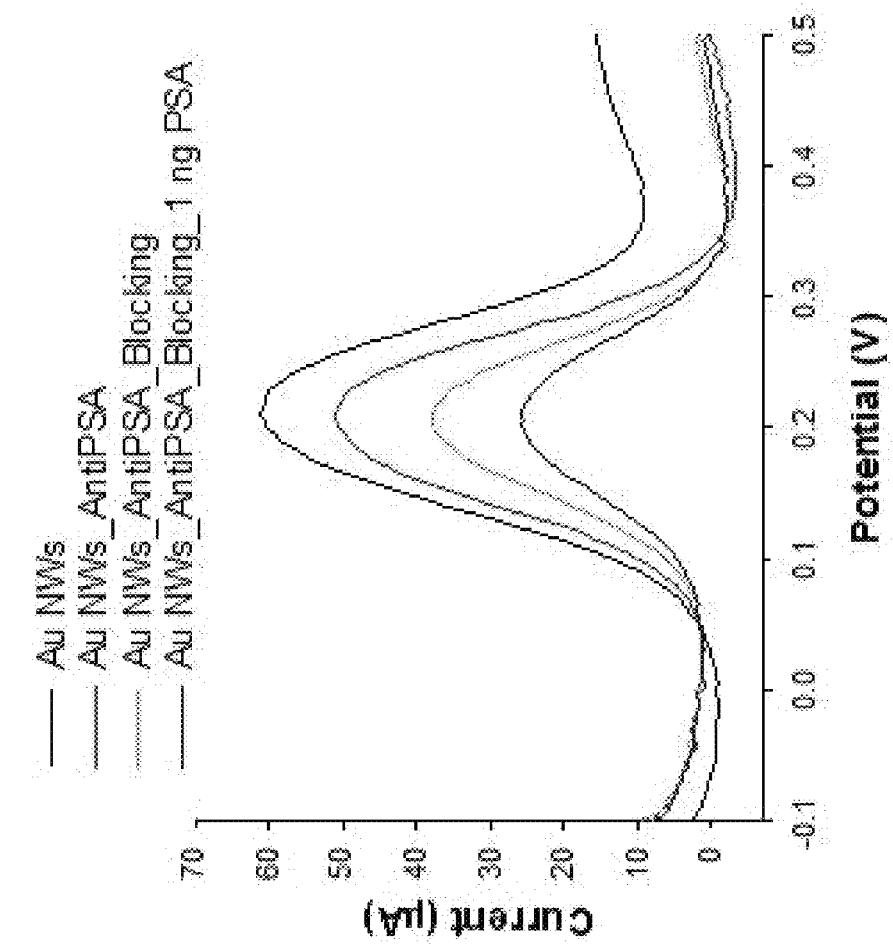
FIG. 10 illustrates a change in current measured by DPV after an anti-PSA is added to gold nanowires (Au NWs) and blocked by BSA and then 1 ng of the anti-PSA is added.
Figure 11:
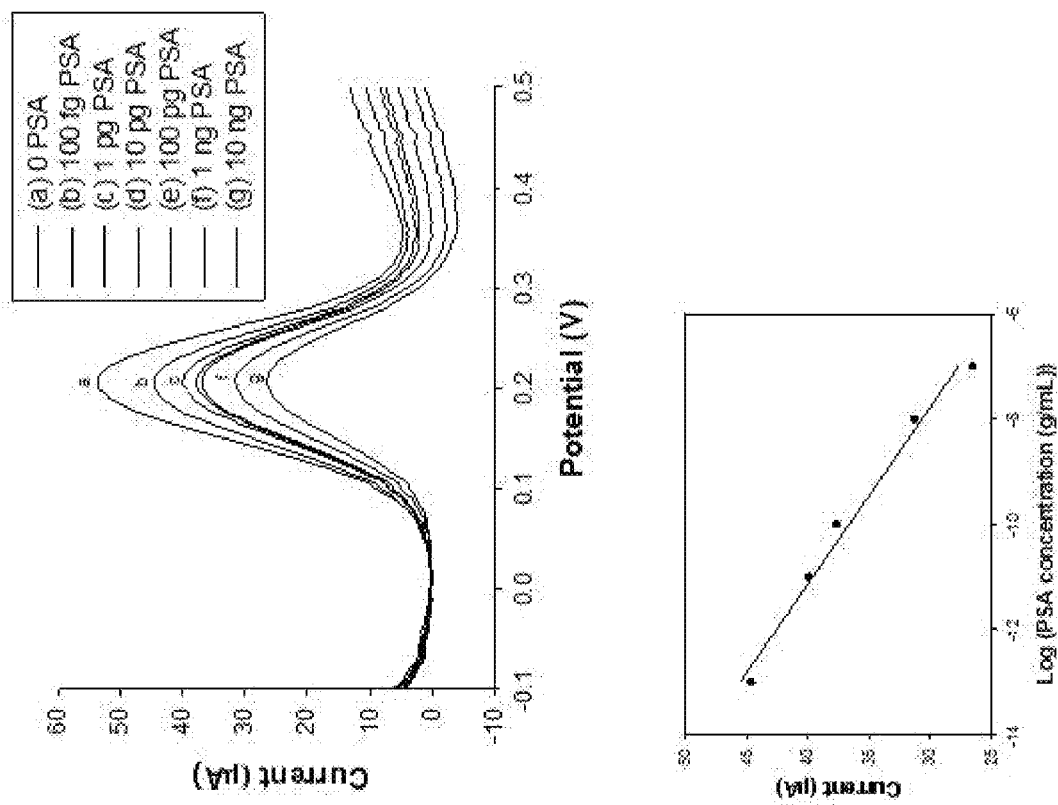
FIG. 11 shows whether or not an antigen-antibody bond on a surface of a gold nanowire interrupts a flow of electrons and also provides a graph showing a degree of interrupting a flow of electrons along with an increase in amount of antigens.

Further, regarding a change in current depending on a change in amount of the PSA as shown in FIG. 10, the highest current value appeared when an amount of the PSA was 0, and the lowest current value of 27.5 μA appeared when an amount of the PSA was 10 ng. Therefore, as expected, it could be seen that an antigen-antibody bond on a surface of a gold nanowire interrupted a flow of electrons.

Experimental Example 5

The present inventors conducted an experiment as follows in order to demonstrate a specific response of an anti-PSA-doped Ppy film to only a sample containing PSA.

Anti-PSA was added to gold nanowires (Au NWs), followed by blocking with BSA. Then, the present inventors separately added 10 ng of PSA, 10 ng of ascorbic acid (AA), 10 ng of IgG, and 10 ng of BSA and measured a change in current.

Figure 12:
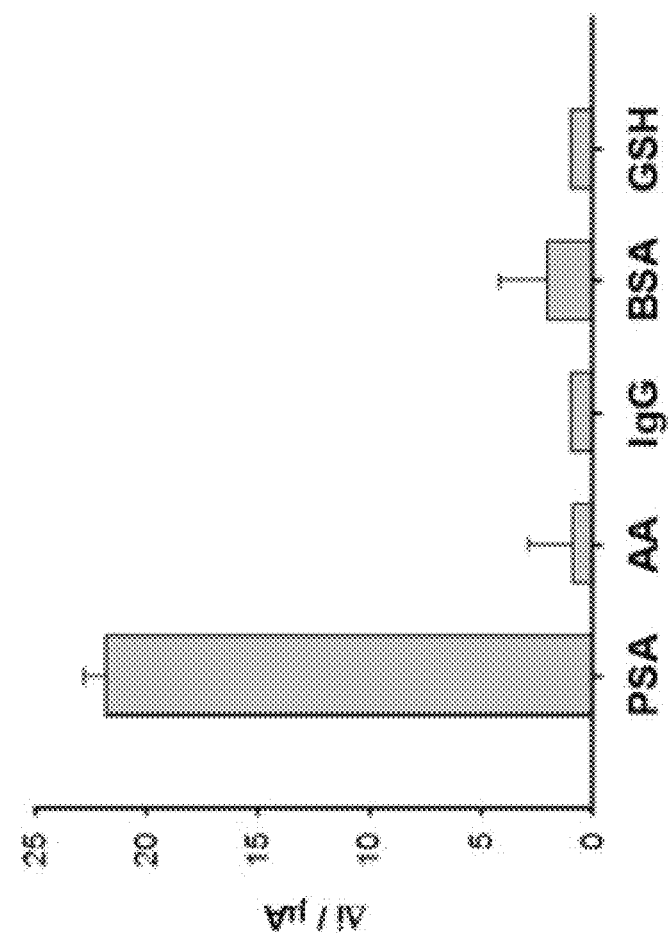
FIG. 12 shows whether or not a film in which an anti-PSA is added to a gold nanowire (Au NW) and blocked by BSA reacts only with a PSA.

According to the experimental result, as shown in FIG. 12, when the PSA was added, a current value was 20 µA. When the AA, the IgG, and the BSA were added separately, a current value was as low as 4 µA, or even less. From this result, it could be seen that an anti-PSA-doped Ppy film according to the present invention showed a response specific to PSA only.

Experimental Example 6

The present inventors conducted an impedance experiment in order to measure a change in current of an anti-PSA-doped Ppy film depending on an amount of PSA.

A line a represents a control sample of a gold nanowire only, a line b represents a Ppy sample containing a gold nanowire doped with anti-PSA, a line c represents a Ppy sample containing a gold nanowire doped with anti-PSA and blocked by BSA, and a line d represents a Ppy sample containing a gold nanowire doped with anti-PSA, blocked by BSA, and added with 1 ng of PSA.

Figure 13:
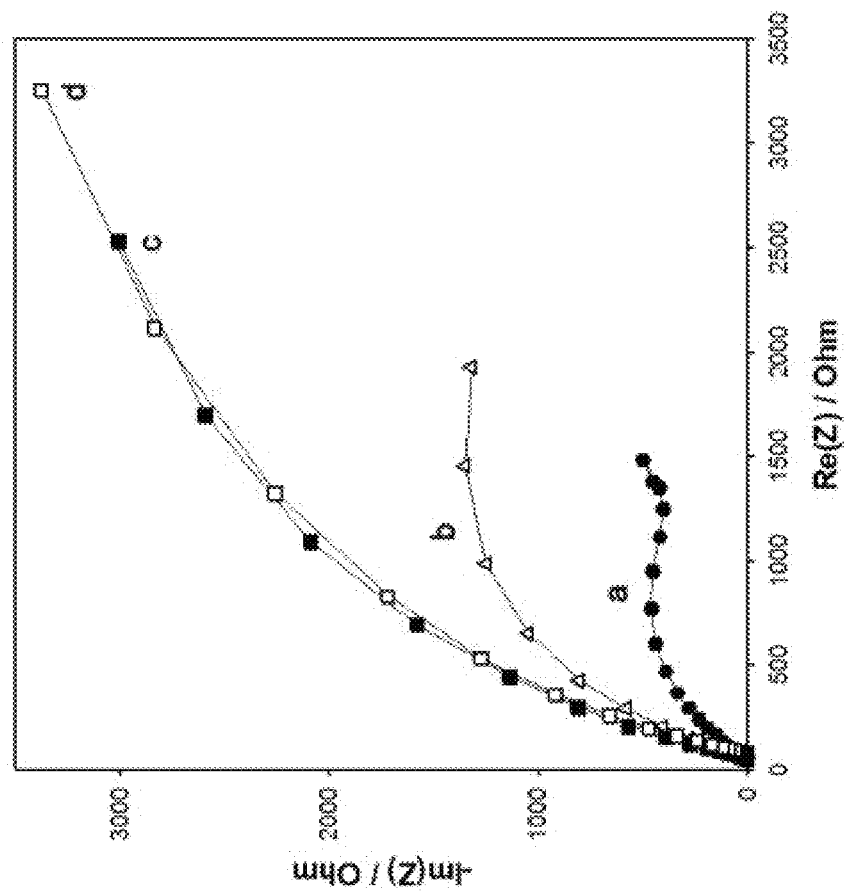
FIG. 13 shows a change in impedance value along with addition of a PSA to a gold nanowire.

According to the experimental result, as shown in FIG. 13, when the PSA was added to the gold nanowire, an impedance value was greatly increased. The sample d showed a value of greater than 3000 Im(Z)/Ohm.

Experimental Example 7

The present inventors conducted an experiment by adding PSA at different concentrations to human serum in order to demonstrate an effect of a current depending on an amount of PSA added on an anti-PSA-doped Ppy film.

Figure 14:
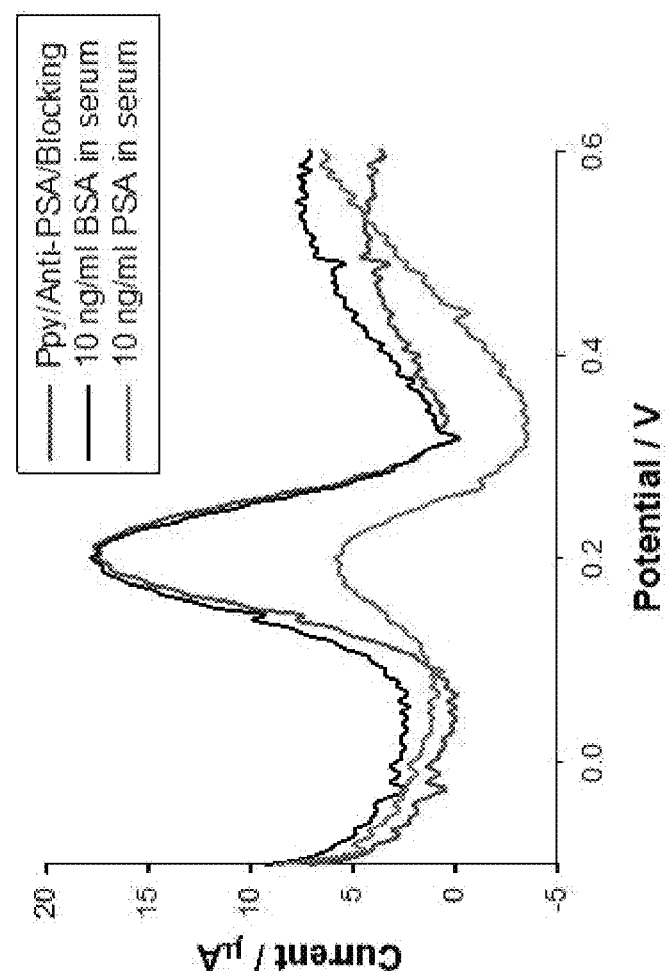
FIG. 14 shows a result of an experiment using human serum, an effect of addition of an anti-PSA to human serum, and also shows that there was a change in current value since a flow of electrons was interrupted by an antigen-antibody reaction which was not made in the presence of BSA but made in the presence of PSA only.

Firstly, 10 ng PSA and 10 ng of BSA were separately dropped to human serum and a change in current was measured. As shown in FIG. 14, when the BSA was added, there was no reaction like a control sample, but only when the PSA was added, an antigen-antibody reaction interrupted and reduced a flow of electrons.

Figure 15:
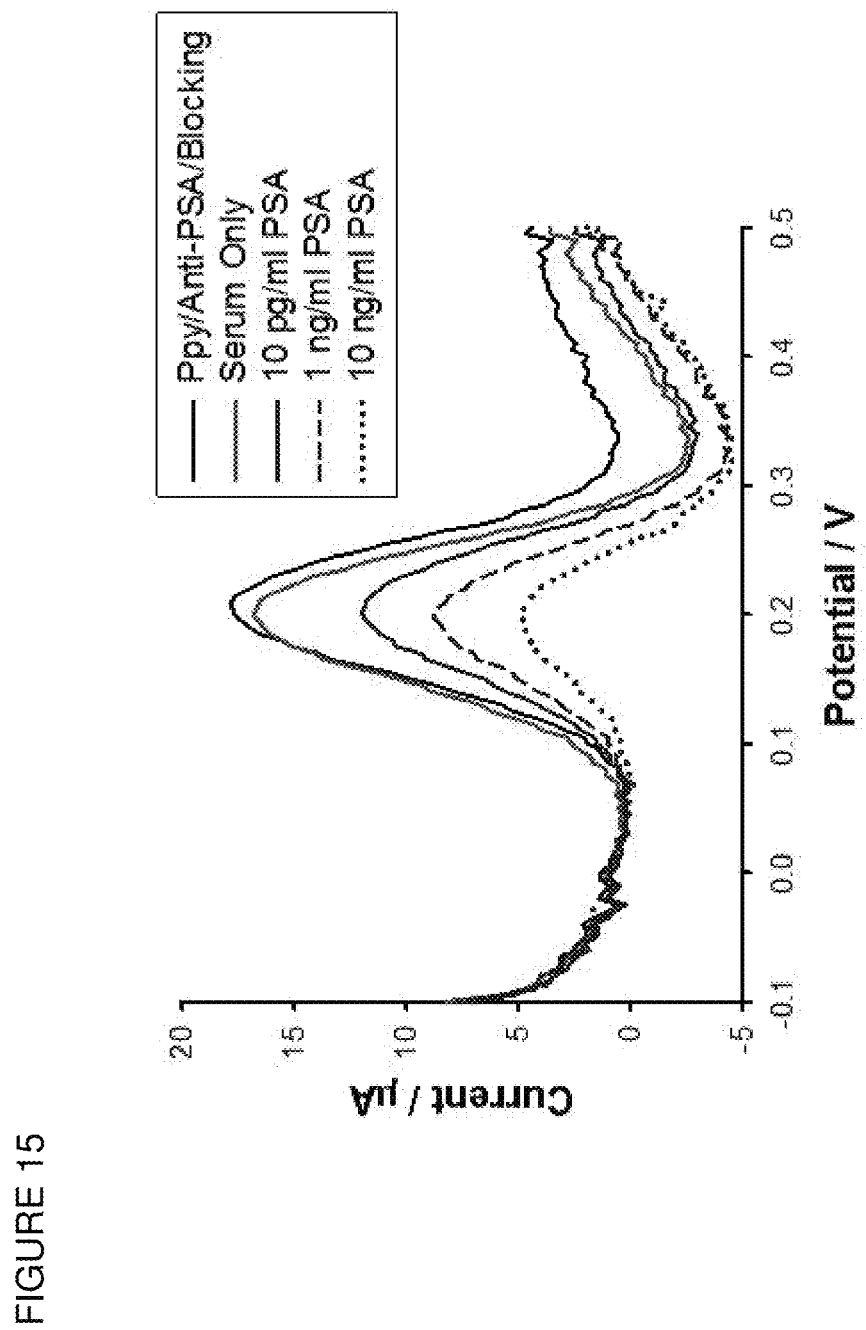
FIG. 15 shows a result of an experiment using human serum, and an effect of a current on an anti-PSA-doped polypyrrole film depending on a change in amount of PSA added to human serum.

Secondly, in order to measure a change in current depending on an amount of PSA added, only human serum, 10 pg/ml of PSA, 1 ng/ml of PSA, and 10 ng/ml of PSA were added separately. As shown in FIG. 15, it could be seen that as an amount of PSA was increased, a current value became decreased.

From this experiment, it could be confirmed that a current value was decreased along with an increase in amount of PSA added to an anti-PSA-doped Ppy film, and as an amount of PSA was increased, a current value was decreased in a uniform manner. Therefore, it is apparent that in the case of manufacturing the present invention as a biosensor, qualification of a target can be carried out stably.

The present invention has been explained with reference to its preferable examples. It would be understood by one of ordinary skill in the art that various changes and modifications may be made without changing technical conception and essential features of the present invention. Therefore, it shall be considered that the above-described examples are illustrative in all aspects and do not limit the present invention. The scope of the present invention is defined by the following claims rather than by the detailed descriptions above. It shall be understood that all modifications and embodiments conceived from the meaning and scope of the claims and their equivalents are included in the scope of the present invention.

What is claimed is:

1. A method for detecting and collecting a Circulating Tumor Cell (CTC) in a sample, comprising:
    contacting the sample with a doped composition comprising a dopant doped within a conducting polymer to detect the CTC in the sample, and
    applying a negative electric field to the doped composition to naturally separate the dopant with the CTC,
    wherein the dopant is doped within the conducting polymer during electropolymerization to form the doped composition and naturally separates from the polymer when the negative electric field is applied;
    the doped composition comprises an antibody bonded to the conducting polymer via a linker comprising a single or multiple linking body/bodies, the linking body comprising biotin and streptavidin, and the doped composition is not a porous film;
    the conducting polymer is polypyrrole,
    the doped composition has a nanowire structure, and
    the dopant is connected to the linker to control the release of the antibody with CTC.

2. The method for detecting and collecting a CTC of claim 1, wherein the antibody is an anti-EpCAM (Epithelial Cell Adhesion Molecule), an anti-PSA (Prostate-Specific Antigen: KLK3 (Kallikrein)), an anti-PSMA (Prostate-Specific Membrane Antigen), an anti-PSCA (Prostate Stem Cell Antigen), an anti-STEAP (Six Transmembrane Epithelial Antigen of the Prostate), an anti-hTERT (human TElomerase Reverse Transcriptase), an anti-WT1 (Wilms tumor 1), an anti-MAGE (Melanoma Antigen Family A)-A2, an anti-5T4(oncofetal antigen 5T4), an anti-MAGE-A3, an anti-MUC1 (Mucin 1, cell surface associated), an anti-Her-2/neu (human epidermal growth factor receptor 2), an anti-CEA (Carcinoembryonic Antigen), an anti-survivin, an anti-MAGE-C1, or an anti-MAGE-C2.

3. The method for detecting and collecting a CTC of claim 1, wherein the linker comprises more than 1 to 50 linking bodies comprised of biotin and streptavidin.

4. The method for detecting and collecting a CTC of claim 1, wherein the composition is attached onto a surface of gold (Au), platinum (Pt), silver (Ag), copper (Cu), iron (Fe), or ITO (Indium Tin Oxide).

5. The method for detecting and collecting a CTC of claim 1, further comprising measuring a change in an electric current.

* * * * *